(12) United States Patent
Akiyama et al.

(10) Patent No.: US 11,402,377 B2
(45) Date of Patent: Aug. 2, 2022

(54) MEMBRANE CARRIER FOR LIQUID SAMPLE TEST KIT, LIQUID SAMPLE TEST KIT, AND MEMBRANE CARRIER

(71) Applicant: DENKA COMPANY LIMITED, Tokyo (JP)

(72) Inventors: Yuto Akiyama, Tokyo (JP); Kenji Monden, Tokyo (JP)

(73) Assignee: DENKA COMPANY LIMITED, Tokyo (JP)

( * ) Notice: Subject to any disclaimer, the term of this patent is extended or adjusted under 35 U.S.C. 154(b) by 0 days.

(21) Appl. No.: 16/770,538

(22) PCT Filed: Dec. 10, 2018

(86) PCT No.: PCT/JP2018/045368
§ 371 (c)(1),
(2) Date: Jun. 5, 2020

(87) PCT Pub. No.: WO2019/117103
PCT Pub. Date: Jun. 20, 2019

(65) Prior Publication Data
US 2021/0172943 A1 Jun. 10, 2021

(30) Foreign Application Priority Data
Dec. 11, 2017 (JP) .............................. JP2017-236605

(51) Int. Cl.
*G01N 33/543* (2006.01)
*B01L 3/00* (2006.01)

(52) U.S. Cl.
CPC .. *G01N 33/54393* (2013.01); *B01L 3/502746* (2013.01); *B01L 3/502761* (2013.01);
(Continued)

(58) Field of Classification Search
CPC ......... B01L 3/502746; B01L 3/502761; B01L 2300/0816; B01L 2400/0406; B01L 3/502; B01L 3/5027; G01N 33/54366
See application file for complete search history.

(56) References Cited

U.S. PATENT DOCUMENTS 4,789,628 A    12/1988    Nayak ............................... 435/7
5,420,016 A  *   5/1995    Boguslaski .............. C12Q 1/04
                                                                        106/2
(Continued)

FOREIGN PATENT DOCUMENTS

JP           4597664 B2     10/2010
JP      2012-524894 A     10/2012
(Continued)

OTHER PUBLICATIONS

International Search Report dated Mar. 12, 2019, issued by the Japanese Patent Office in corresponding application PCT/JP2018/045368.
(Continued)

*Primary Examiner* — Melanie Brown
*Assistant Examiner* — Jennifer H. Tieu
(74) *Attorney, Agent, or Firm* — Stein IP, LLC (57) ABSTRACT

A membrane carrier for a liquid sample test kit that detects a substance to be detected in a liquid sample, the membrane carrier including at least one integrally-molded flow path capable of transporting the liquid sample, in which a microstructure that causes a capillary action for transporting the liquid sample is provided on a bottom surface of the flow path, and the microstructure has two or more peak positions at which a height becomes maximum per one repeating unit structure.

10 Claims, 7 Drawing Sheets

(52) U.S. Cl.
CPC . *G01N 33/54366* (2013.01); *G01N 33/54386* (2013.01); *B01L 2300/0816* (2013.01); *B01L 2400/0406* (2013.01)

(56) References Cited

U.S. PATENT DOCUMENTS

| | | | | |
|---|---|---|---|---|
| 7,223,364 | B1* | 5/2007 | Johnston | B01L 3/5023 422/502 |
| 9,347,931 | B2* | 5/2016 | Killard | G01N 33/86 |
| 2006/0239859 | A1* | 10/2006 | Ohman | B01L 3/502746 422/400 |
| 2011/0114859 | A1* | 5/2011 | Amako | G01N 21/55 257/E31.127 |
| 2015/0233907 | A1 | 8/2015 | Gupta et al. | |

FOREIGN PATENT DOCUMENTS

| | | |
|---|---|---|
| JP | 2013-113633 A | 6/2013 |
| JP | 2014-62820 A | 4/2014 |
| JP | 2014-510925 A | 5/2014 |
| JP | 5609648 B2 | 9/2014 |
| JP | 5821430 B2 | 10/2015 |
| JP | 2016-11943 A | 1/2016 |
| JP | 2016-179198 A | 10/2016 |
| WO | WO 2015/098784 A1 | 7/2015 |
| WO | WO 2016/051974 A1 | 4/2016 |
| WO | WO 2016/098740 A1 | 6/2016 |

OTHER PUBLICATIONS

Japanese Office Action dated Jan. 25, 2022, issued to corresponding Japanese Application No. 2019-559636.

* cited by examiner

BIRD'S-EYE VIEW

LINE A-A SECTIONAL VIEW

MEMBRANE CARRIER FOR LIQUID SAMPLE TEST KIT, LIQUID SAMPLE TEST KIT, AND MEMBRANE CARRIER

CROSS-REFERENCE TO RELATED APPLICATIONS

This application is a national stage of International Application No. PCT/JP20181045368, filed Dec. 10, 2018, which claims the benefit of Japanese Application No. 2017-236605, filed Dec. 11, 2017, in the Japanese Patent Office, the disclosures of which are incorporated herein by reference.

TECHNICAL FIELD

The present invention relates to a membrane carrier for a liquid sample test kit, a liquid sample test kit, and a membrane carrier.

BACKGROUND ART

In recent years, a Point of Care Test (POCT) reagent, which measures an affliction of an infectious disease, pregnancy, a blood glucose level, and the like by using an antigen-antibody reaction and the like, has attracted attention. The POCT reagent has characteristics that a result can be determined in a short time, a use method is simple, and the cost is low. With these characteristics, the POCT reagent is frequently used for medical examinations and periodic medical examinations at a stage where the symptoms are mild, and is an important medical examination tool in home medical care, which is expected to increase in the future.

In many POCT reagents, a determination is made by introducing a liquid sample such as blood into a test kit and detecting a specific substance to be detected contained therein. As a method for detecting a specific substance to be detected from the liquid sample, an immunochromatography method is often used. An immunochromatography method refers to a technique in which a substance to be detected and a label are bound while a liquid dropped on a membrane carrier of a test kit moves on the membrane carrier, these specifically bind to a substance (hereinafter, referred to as detection substance) immobilized in the test kit, and a change in color or mass generated as a result is detected. The detection substance may be referred to as a reagent.

As a technique of detecting a substance to be detected, a method of detecting a change in color caused by using colored latex particles, fluorescent latex particles, metal colloidal particles, and the like as a label via an optical measurement device such as an absorbance measurement device is well known.

As a POCT reagent for optically determining the change in color, a lateral flow type kit using a nitrocellulose membrane is often used (Patent Document 1). The nitrocellulose membrane has a large number of fine holes having a diameter of about several μm, and the liquid sample moves in the holes by capillary force.

However, since the nitrocellulose membrane is derived from a natural product, and a pore diameter and a way of connecting the pores are not uniform, there occurs a difference in a flow rate of the liquid sample flowing in each membrane. Patent Document 2 discloses a technique of controlling a flow rate, but does not solve an essential problem that a pore diameter or the way of connecting the pores are not uniform. In a case where a difference occurs in the flow rates, the time required to detect a substance to be detected is also changed, and as a result, the substance to be detected may be erroneously determined as non-detection before binding occurs.

In order to solve the above-mentioned problem, a technique of artificially preparing a fine flow path has been devised (Patent Documents 3 to 7). In a case of using the technique, it is possible to prepare a membrane carrier having a uniform structure, and thus it is possible to decrease a possibility that a substance to be detected is erroneously determined as non-detection before binding occurs.

In the above patent documents, the flow path structure in the system is uniform, and thus there is no limit in detection performance. Patent Document 8 discloses a technique for improving the detection performance at a time of using an artificial fine flow path, in which a groove-shaped flow path for the purpose of flow rate control, is combined with a pillar-shaped flow path for the purpose of improving sensitivity.

RELATED DOCUMENT

Patent Document

[Patent Document 1] Japanese Unexamined Patent Publication No. 2014-062820
[Patent Document 2] International Publication No. WO 2016/051974
[Patent Document 3] Japanese Patent No. 4597664
[Patent Document 4] PCT Japanese Translation Patent Publication No. 2012-524894
[Patent Document 5] Japanese Patent No. 5609648
[Patent Document 6] Japanese Unexamined Patent Publication No. 2016-011943
[Patent Document 7] Japanese Unexamined Patent Publication No. 2013-113633
[Patent Document 8] Japanese Patent Application No. 5821430
[Patent Document 9] International Publication No. WO 2016/098740

SUMMARY OF THE INVENTION

Technical Problem

However, in a case where the technology disclosed in the related art is used, many substances to be detected or labels in the liquid sample pass through the groove-shaped flow path or the pillar structures, and a reaction rate with the detection substances immobilized to a surface portion of the microstructures was decreased. Due to this cause, the detection sensitivity became low.

Patent Document 9 discloses a membrane carrier for a liquid sample test kit that detects a substance to be detected in a liquid sample, in which at least one flow path capable of transporting the liquid sample is provided, and the microstructure that generates a capillary action for transporting the liquid sample is provided on a bottom surface of the flow path. However, Patent Document 9 does not describe that the microstructure has two or more peak positions.

In view of the above problems, an object of the present invention is to provide a membrane carrier for a test kit that can perform highly sensitive determination.

That is, the present invention is as follows.

(1) A membrane carrier for a liquid sample test kit that detects a substance to be detected, in a liquid sample, the membrane carrier including: at least one integrally-molded flow path capable of transporting the liquid sample, in which a microstructure that causes a capillary action for transporting the liquid sample is provided on a bottom surface of the flow path, and in which the microstructure is a structure having two or more peak positions at which the height becomes maximum per one repeating unit structure.

(2) The membrane carrier for a liquid sample test kit according to (1), in which the structure having two or more peak positions at which a height becomes maximum per one repeating unit structure is provided only in a portion of the flow path.

(3) The membrane carrier for a liquid sample test kit according to (1) or (2), a height of the microstructure, which is a minimum value in a region between the peak positions in the microstructure, is equal to or more than ⅛ and equal to or less than ⅞ of the height at the peak positions.

(4) The membrane carrier for a liquid sample test kit according to any one of (1) to (3), further including: a detection zone for detecting the substance to be detected in the liquid sample.

(5) The membrane carrier for a liquid sample test kit according to (4), in which, in a case where the substance to be detected is detected in the detection zone, the detection can be confirmed by an optical technique.

(6) The membrane carrier for a liquid sample test kit according to any one of (1) to (5), in which a label having an antibody specifically reacting with the substance to be detected in the liquid sample or an antigen-binding fragment thereof is provided in at least a portion of the membrane carrier for a liquid sample test kit so as to react with the substance to be detected, and in which means capable of being confirmed by an optical technique is a change in color, and the change in color is caused by the label bound to the substance to be detected.

(7) The membrane carrier for a liquid sample test kit according to (6), in which the label is a particle to which the antibody or the antigen-binding fragment is bound.

(8) The membrane carrier for a liquid sample test kit according to (7), in which the particle is at least one kind from the group consisting of a colored latex particle and a fluorescent latex particle.

(9) A membrane carrier for a liquid sample test kit that immobilizes, in a detection zone of the membrane carrier for a liquid sample test kit according to (4) or (5), a detection substance causing a change in color capable of confirming the detection by an optical technique, in a case where the substance to be detected is detected in the detection zone.

(10) A liquid sample test kit having the membrane carrier for a liquid sample test kit according to any one of (1) to (9).

(11) A membrane carrier that detects a substance to be detected in a liquid sample, the membrane carrier including: a flow path capable of transporting the liquid sample, in which the microstructure is provided on a bottom surface of the flow path, and in which the microstructure is a structure having two or more peak positions at which a height becomes maximum per one repeating unit structure.

The membrane carrier for a liquid sample test kit of the present invention can perform a highly sensitive test.

BRIEF DESCRIPTION OF THE DRAWINGS

The objects, other objects, features, and advantages will become more apparent from the preferred embodiments described below and the accompanying drawings.

DESCRIPTION OF EMBODIMENTS

Hereinafter, embodiments of the present invention will be described with reference to the drawings. In all the drawings, like components are denoted, by common reference numerals, and description thereof will not be repeated. In addition, the drawing is a schematic view, and does not match the actual dimensional ratio.

The membrane carrier for a liquid sample test kit of the present embodiment refers to a membrane carrier for a liquid sample test kit that detects a substance to be detected in a liquid sample, for example.

Figure 8:
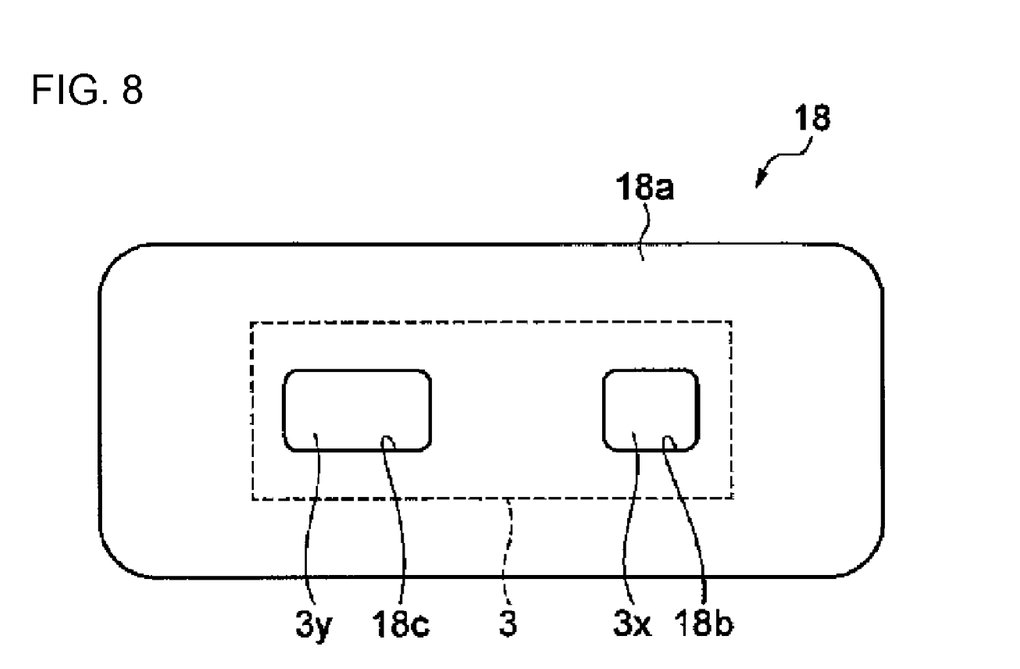
FIG. 8 is an example of an embodiment according to the present invention, and is a schematic top view of a test kit.

The test kit according to the present embodiment detects a substance to be detected in a liquid sample. For example, as illustrated in FIG. 8, the test kit 18 includes a membrane carrier 3 and a housing 18a that houses the membrane carrier 3. On a surface of the membrane carrier 3, there are a dropping zone 3x where a liquid sample is dropped, and a detection zone 3y for detecting a substance to be detected in the liquid sample. The dropping zone 3x is exposed at a first opening 18b of the housing 18a. The detection zone 3y is exposed, at a second opening 18c of the housing 18a. At least one flow path transporting a liquid sample is provided in the membrane carrier 3, and a microstructure is provided on a bottom surface of the flow path. The microstructure is positioned at least between the dropping zone 3x and the detection zone 3y. A microstructure may be present over the entire surface of the membrane carrier 3.

Figure 9:
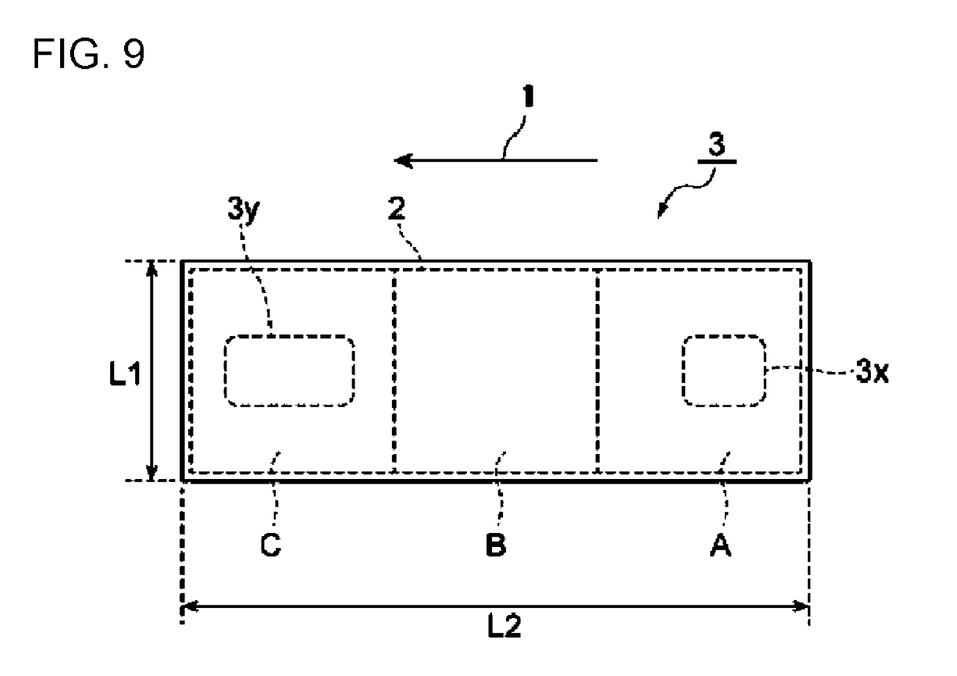
FIG. 9 is an example of an embodiment according to the present invention, and is a schematic top view of the membrane carrier.

FIG. 9 is a schematic top view of the membrane carrier 3. As illustrated in FIG. 9, the membrane carrier 3 has at least one flow path 2 transporting a liquid sample. The flow path 2 is preferably provided by integral molding. A microstructure is provided on the bottom surface of the flow path 2 (not illustrated, details will be described later). The microstructure is positioned at least between the dropping zone 3x and the detection zone 3y. The microstructure may be provided over the entire surface of the membrane carrier 3. The entire surface of the membrane carrier 3 may be the flow path 2 of the liquid sample. The microstructure causes capillary action. By a capillary action of the microstructure, the liquid sample is transported (along a transporting direction 1) from the dropping zone 3x to the detection zone 3y via the microstructure. In a case where the substance to be detected in the liquid sample is detected in the detection zone 3y, color of the detection zone 3y changes.

The entire shape of the membrane carrier 3 is not particularly limited, but may be, for example, a polygon such as a square, a circle, or an ellipse. In a case where the membrane carrier 3 is a square, a vertical width (length in a short-side direction) L1 of the membrane carrier 3 may be equal to or more than 2 mm and equal to or less than 100 mm, for example, and a horizontal width (length in a long-side direction) L2 of the membrane carrier 3 may be equal to or more than 2 mm and equal to or less than 100 mm, for example. A thickness of the membrane carrier excluding a height of the microstructure may be equal to or more than 0.1 mm and equal to or less than 10 mm, for example.

For example, the microstructure is provided so as to change along the transporting direction 1 of the liquid sample. In other words, the membrane carrier 3 has a plurality of regions (first region A, second region B, and third region C in order from the dropping zone side) provided along the transporting direction 1 of the liquid sample, and regions adjacent to each other (first region A and second region B, second region B and third region C) have microstructures different from each other.

The entire surface of the membrane carrier 3 may be a flow path of a liquid sample. The microstructure causes capillary action. By the capillary action of the microstructure, the liquid sample is transported from the dropping zone 3x to the detection zone 3y via the microstructure. In a case where the substance to be detected in the liquid sample is detected in the detection zone 3y, color of the detection zone 3y changes. As illustrated in FIGS. 1 to 6, the microstructure is an entirety (aggregate) of convex portions. That is, the microstructure includes a flat portion corresponding to the bottom surface of the flow path of the liquid sample, and a plurality of convex portions protruding from the flat portion. By the capillary action, a space between the plurality of convex portions functions as a flow path transporting the liquid sample along the surface of the membrane carrier 3. In other words, a void in the microstructure functions as a flow path transporting the liquid sample along the surface of the membrane carrier 3 by the capillary action. The plurality of convex portions may be regularly or translationally arranged in line on the surface of the membrane carrier.

A test method of a liquid sample according to an aspect of the present embodiment is a test method using the test kit 18.

For example, the test method may include: dropping a liquid sample onto the dropping zone 3x on the surface of the membrane carrier 3; transporting the liquid sample from the dropping zone 3x to the detection zone 3y via a microstructure by a capillary action exhibited by the microstructure formed on the surface of the membrane carrier 3; and, in the transporting process, binding a substance to be detected in the liquid sample to a label, binding the substance to be detected to a reagent (hereinafter, referred to as detection substance) immobilized on the detection zone 3y, and optically determining the presence or absence of a change in color (coloring of the label) in the detection zone 3y.

The label refers to a substance that binds to a substance to be detected. Among the labels, particles are preferable. In the test method, the method of immobilizing a label is not particularly limited. For example, a label may be immobilized on a member of a kit, or may be immobilized to a portion of the membrane carrier 3, for example.

For example, a test method using the test kit 18 includes: mixing a liquid sample with particles and binding a substance to be detected in the liquid sample to the particles to prepare a label (hereinafter, referred to as labeled particles in some cases); dropping the mixed liquid sample onto the dropping zone 3x on the surface of the membrane carrier 3; transporting the liquid sample from the dropping zone 3x to the detection zone 3y via the microstructure by the capillary action exhibited by the microstructure formed on the surface of the membrane carrier 3; and binding the substance to be detected to a reagent immobilized in the detection zone 3y and optically determining the presence or absence of a change in color (coloring of labeled particles) in the detection zone 3y.

In the test method, the method of, mixing a liquid sample with labeled particles is not particularly limited. For example, the method may be a method of adding a liquid sample to a container containing labeled particles, for example, a liquid containing labeled particles and a liquid sample may be mixed with each other, for example. For example, a filter may be interposed between dropping ports of a container in which a liquid sample is placed, and the labeled particles may be immobilized in the filter, for example.

The microstructure or the membrane carrier of the liquid sample test kit of the present embodiment may be formed of a thermoplastic plastic. In other words, by processing a membrane-shaped base formed of a thermoplastic plastic, it is possible to prepare a membrane carrier having a microstructure. Examples of a processing method include thermal imprinting, UV imprinting, injection molding, etching, photolithography, mechanical cutting, and laser processing, for example. Among these, as a technique of performing accurate processing at a low cost, thermal imprinting, on thermoplastic plastic is suitable. Examples of the thermoplastic plastic include a polyester-based resin, a polyolefin-based resin, a polystyrene-based resin, a polycarbonate-based resin, a fluorine-based resin, and an acrylic-based resin. Specific examples thereof include polyethylene terephthalate (PET), cycloolefin polymer (COP), polypropylene (PP), polystyrene (PS), polycarbonate (PC), polyvinylidene fluoride (PVDF), polymethyl methacrylate (PMMA), and the like.

The microstructure (hereinafter, referred to as a convex portion in some cases) can be formed by having a convex portion. It is preferable to have a plurality of convex portions. The shape of the microstructure is a shape having two or more peak positions at which the height becomes maximum per one repeating unit structure. The shape of the microstructure is preferably a shape having five or less peak positions at which the height becomes a maximum, more preferably a shape having three or less peak positions, and particularly preferably two peak positions per one repeating unit structure.

One repeating unit structure mentioned herein usually refers to one convex portion.

Figure 1:
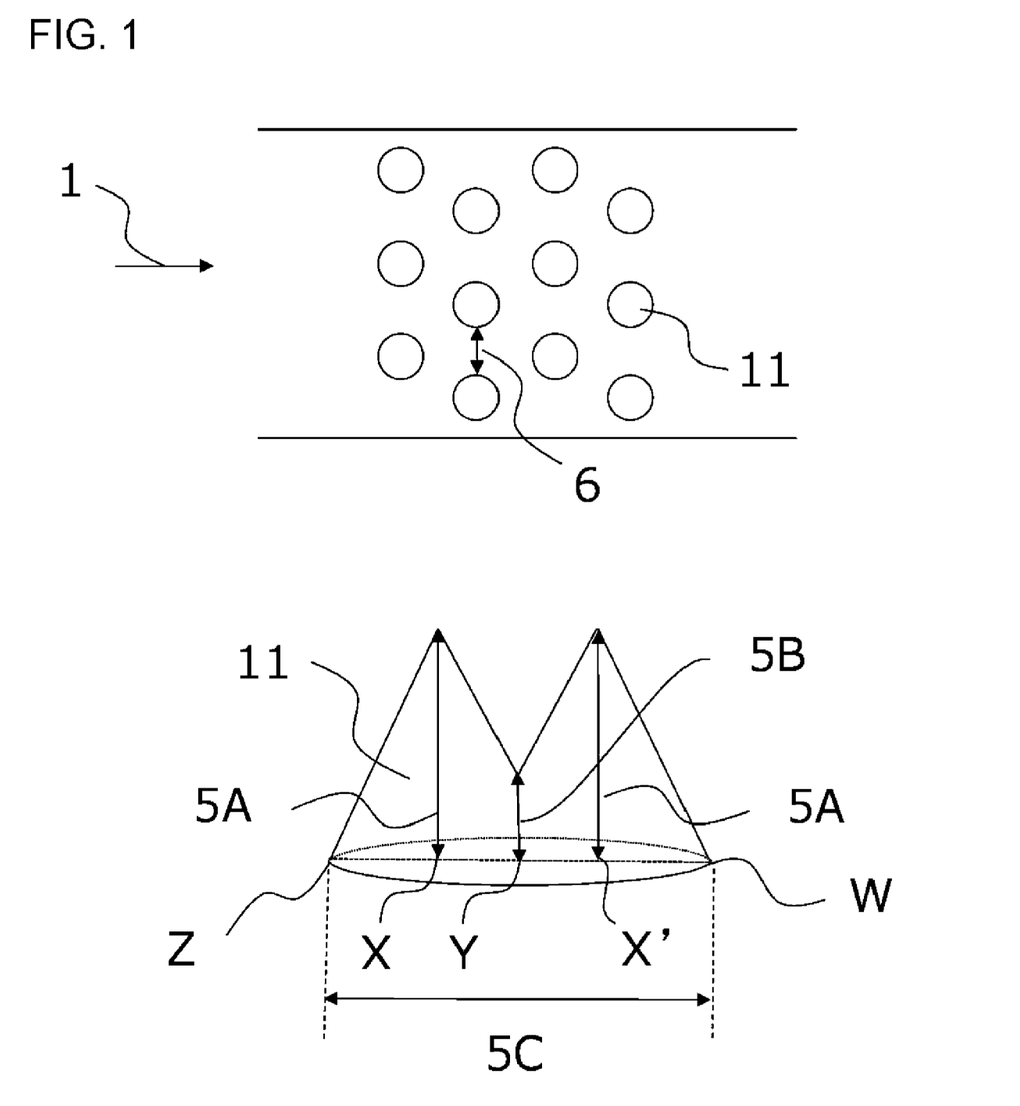
FIG. 1 is an example of an embodiment according to the present invention, and is a bird's-eye view of a microstructure.
Figure 2:
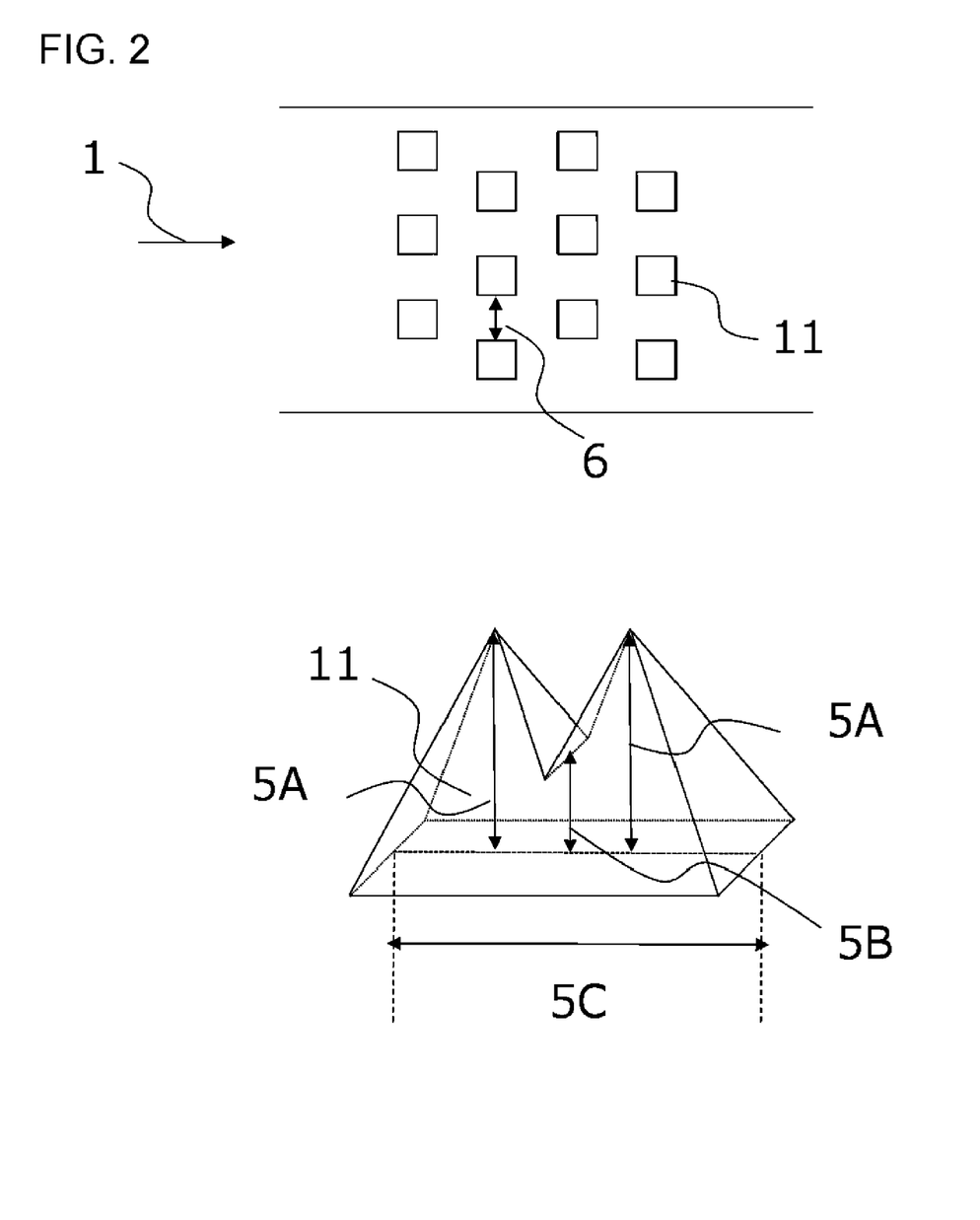
FIG. 2 is an example of an embodiment according to the present invention, and is a bird's-eye view of the microstructure.
Figure 3:
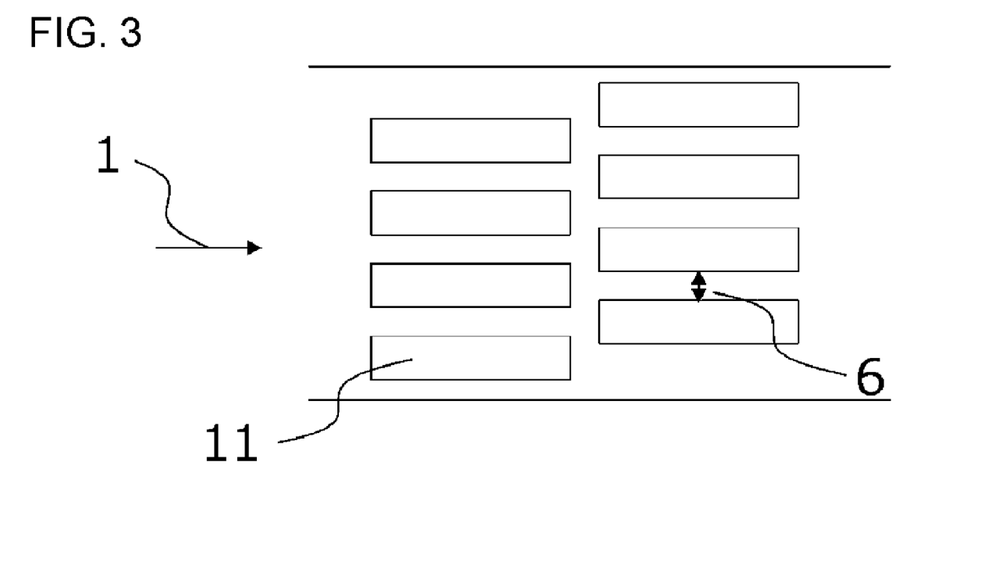
FIG. 3 is an example of an embodiment according to the present invention, and are bird's-eye views of the microstructure.

For example, as illustrated in FIG. 1, the microstructure may be a structure in which two cones are connected. For example, as illustrated in FIG. 2, the microstructure may be a structure in which two quadrangular pyramids are connected. For example, as illustrated in FIG. 3, the microstructure may be a structure in which two horizontally arranged triangular prisms (triangular prisms arranged so that one side surface (quadrangular surface) of the triangular prism is in contact with the membrane carrier) are continuous. From a viewpoint that, in a case where the entire surface area from a bird's-eye view of the microstructure can be visually recognized, a change in color at a time of detecting a substance to be detected is easily optically detected, among these, a complex of conical bodies such as cone and polygonal pyramid, that is, a conical body having two or more peak positions is preferable. Among the conical bodies, cones are preferable. The liquid sample is transported to the microstructure or the membrane carrier of the test kit from the transporting direction 1 in which the liquid sample flows.

Figure 6:
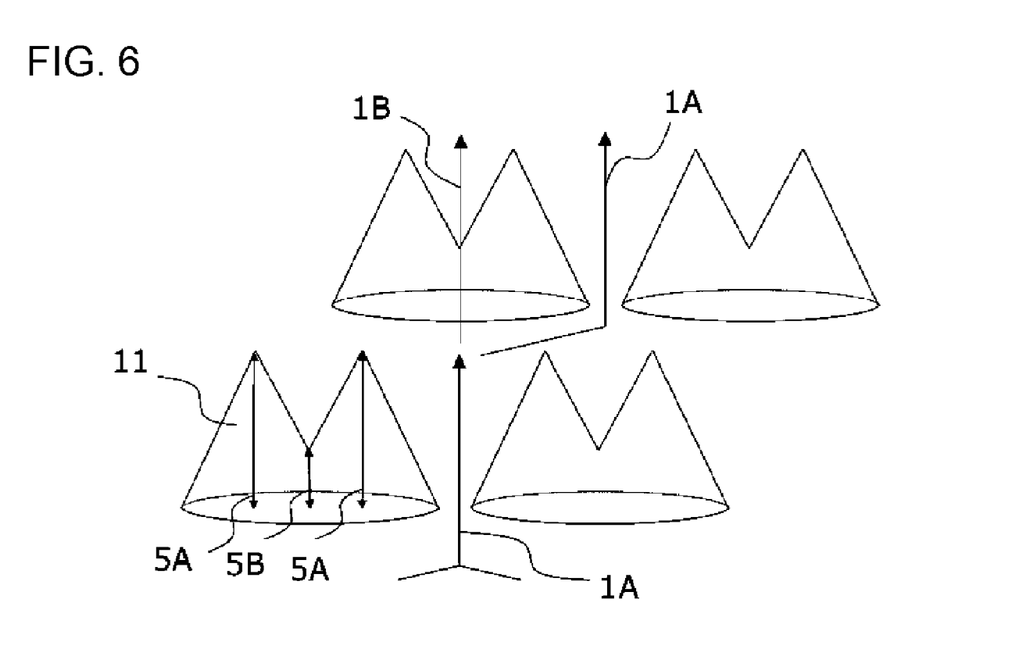
FIG. 6 is an example of an embodiment according to the present invention, and are schematic views indicating the flow in the microstructure.

As illustrated in FIG. 6, in a case where the shape of the microstructure is a shape having two or more peak positions at which the height becomes the maximum per one repeating unit structure, a branch is generated into a flow 1B traveling in the gap between the peak positions from a flow 1A traveling in the gap between different structures, and in the process, stirring of the substance to be detected and the label in relation to a height direction in the liquid sample is promoted, and a reaction rate between the substance to be detected and the label is improved. Therefore, the performance of the test kit is improved. In a case where the microstructure of the detection zone is the structure, the substance to be detected and the label collide with a surface portion of the microstructure by the flow 1B traveling in the gap at the peak position. As the detection substance is immobilized on the surface portion of the detection zone, and the substance to be detected and the label collide therewith, improvement in detection sensitivity can be achieved.

As described above, a region in which the shape of the microstructure has two or more peak positions at which the height becomes maximum per one repeating unit structure may be a part of the entire microstructure. Only the detection zone where the effect of improving the detection sensitivity by the structure appears most strong is set as the structure, and in other regions, simple structures such as a cone, a pyramid, a truncated cone, a truncated pyramid, a cylinder, a polygonal prism, a hemisphere, a semi-ellipsoid, and the like, for example, set as a conical body having one peak position, and thereby it is possible to improve sensitivity in the detection zone while controlling the entire flow rate.

As described above, in a case where the shape of the microstructure has two or more peak positions at which the height becomes the maximum per one repeating unit structure, a region where the height becomes the minimum in the region between the peak positions occurs. A ratio 5B/5A between a minimum value 5B of the height in this region (hereinafter, referred to as the height of the microstructure which becomes the minimum value) and a higher value 5A (maximum value of the height) among the peak positions that becomes a maximum is preferably equal to or more than 1/8 and equal to or less than 7/8, and more preferably equal to or more than 1/4 and equal to or less than 3/4. Within this range, there occurs a branch from a flow traveling between the structures to a flow traveling in the gap between the peak positions, and the area of the surface portion where the substance to be detected and the label collide with each other is large. Therefore, the detection sensitivity is improved.

As illustrated in FIG. 1, in a case where the microstructure is a structure in which two cones are connected, the following is preferable. A diameter 5C of a bottom surface of a convex portion 11 is preferably a diameter of a bottom surface (circle) of a cone. 5A (the maximum value of the height) is preferably a length of a perpendicular line lowered from the vertex of the cone to the bottom surface. It is preferable that 5B (minimum value of the height) is a length of a perpendicular line lowered from a region point where the height is minimum to the bottom surface. The perpendicular feet X, X' of 5A (maximum value of the height) and the perpendicular foot Y of 5B (minimum value of the height) are preferably on a diameter ZW of the bottom surface (circle). Z and W are intersections of a circumference of the bottom surface (circle) and the diameter. A distance (for example, ZX, WX') between the intersection point of the circumference and the diameter and the perpendicular foot of the maximum value of the height, or a distance (for example, XY, YX') between the perpendicular foot of the maximum value of the height and the perpendicular foot of the minimum value of the height is preferably completely the same.

As illustrated in FIG. 2, in the case where the microstructure is a structure in which two quadrangular pyramids are connected, the following is preferable. The diameter 5C of the bottom surface of the convex portion 11 is a length of a side of the bottom surface (square). The side is preferably a long side. 5A (maximum value of the height) is preferably the length of a perpendicular line lowered from the vertex of the quadrangular pyramid to the bottom surface. It is preferable that 5B (minimum value of the height) is a length of a perpendicular line lowered from a region point where the height is minimum to the bottom surface. The perpendicular foot of 5A (maximum value of the height) and the perpendicular foot of 5B (minimum value of the height) are preferably on the same line on the bottom surface (square).

As illustrated in FIG. 3, in a case where the microstructure is a structure in which two horizontally arranged triangular prisms are continuous, the following is preferable. The diameter 5C of the bottom surface of the convex portion 11 is a length of a side of the bottom surface (square). The side is preferably a short side. It is preferable that 5A (maximum value of the height) is the length of a perpendicular line lowered from a ridge line of the horizontally arranged triangular prism to the bottom surface. It is preferable that 5B (minimum value of the height) is a length of a perpendicular line lowered from a region point where the height is minimum to the bottom surface. The perpendicular foot of 5A (maximum value of the height) and the perpendicular foot of 5B (minimum value of the height) are preferably on the same side of the bottom surface (square).

It is preferable that a foot Y of the perpendicular line of 5B (minimum value of the height) is located at the center or the center of gravity of the bottom surface.

Figure 4:
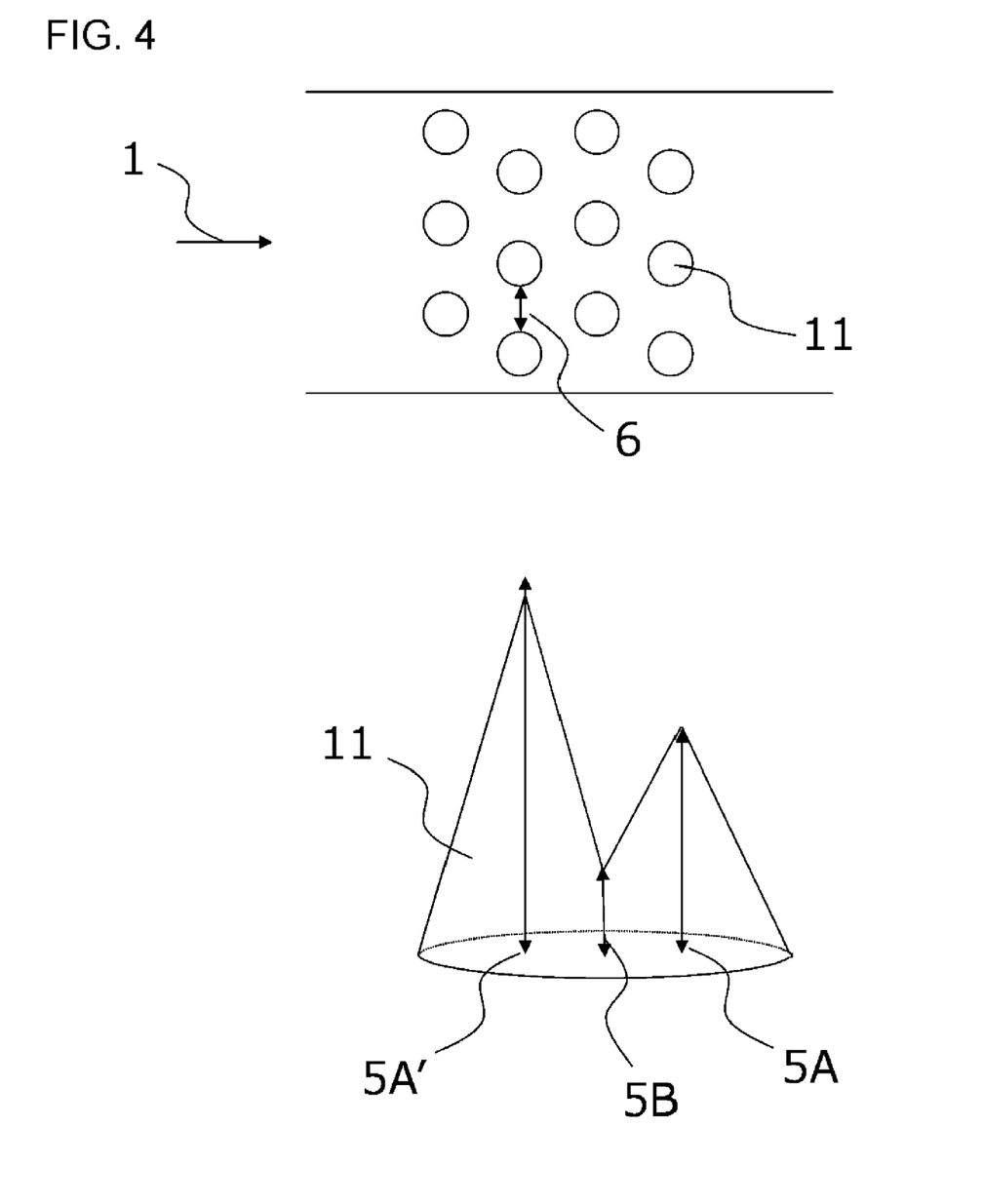
FIG. 4 is an example of an embodiment according to the present invention, and are bird's-eye views of the microstructure.
Figure 5:
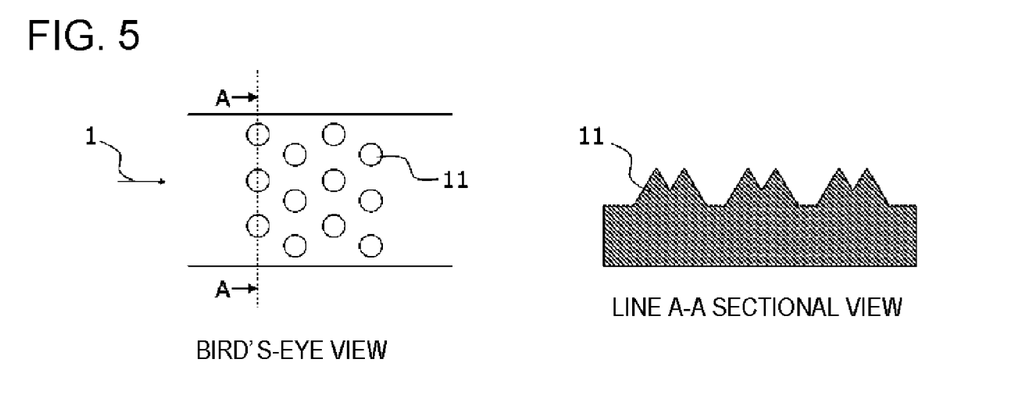
FIG. 5 is an example of an embodiment according to the present invention, and are a bird's-eye view and a sectional view of the microstructure.

The height at the peak position where the height is maximum, of the structure, may be different for each peak position as illustrated in FIG. 4. The ratio (5A'/5A) of the height between the plurality of peak positions is not particularly limited, but is preferably equal to or more than 0.5/1 and equal to or less than 5/1, and more preferably equal to or more than 1/1 and equal to or less than 3/1, from a viewpoint of suppressing damage to the structure at a time of membrane carrier processing.

In a case of a processing method using a mold such as imprinting or injection molding, the conical body is thinner at the top than at the bottom surface. Therefore, a volume to be carved out during mold preparation is smaller than that of a column with the same bottom surface, and thus it is possible to prepare a mold at a low cost.

The microstructure does not need to have a geometrically accurate shape, and may have a rounded corner or fine irregularities on the surface.

FIGS. 1 to 5 illustrate an example of a bird's-eye view and a sectional view of a microstructure provided on a bottom surface of a flow path in the present embodiment.

Examples of the particles according to the present embodiment include colloidal particles and latex particles. The particles may have magnetism or fluorescence. Examples of the colloidal particles include metal colloidal particles such as gold colloidal particles and platinum colloidal particles. Among these, latex particles are preferable from a viewpoint of particle diameter control, dispersion stability, and binding easiness.

From a viewpoint of visibility, the particles are preferably at least one kind of the group consisting of colored particles and fluorescent particles, and the colored particles are more preferable. The colored particles may be any particles as long as the color can be detected with naked eye. The fluorescent particles may contain a fluorescent substance.

Although the material of the latex particles according to the present embodiment is not particularly limited, polystyrene is preferable.

The particles according to the present embodiment bind to an antibody or an antigen thereof specifically reacting with the substance to be detected to prepare a label. The antibody or antigen may be a binding fragment. The binding fragment refers to a fragment that can specifically bind to a substance to be detected, and for example, refers to an antigen-binding fragment of an antibody or an antibody-binding fragment of an antigen, for example. With this, the label can bind to the substance to be detected via the antibody or antigen.

The height at the peak position of the microstructure refers to the height 5A of the convex portion 11. The height at the peak position of the microstructure is not particularly limited, but is preferably 10 to 500 μm, and more preferably 50 to 480 μm, for example. In a case where the height is equal to or more than 10 μm, the volume of the flow path becomes large, and it does not take a long time to develop the liquid sample. In a case where the height is equal to or less than 500 μm, it does not take much time and cost to prepare the microstructure, and the structure can be easily prepared.

A closest distance between the convex portion 11 constituting the microstructure (hereinafter, also referred to as the closest distance between microstructures) 6 is preferably equal to or less than 500 μm, and more preferably equal to or more than 2 μm and equal to or less than 100 μm. The closest distance 6 between the convex portions 11 may change within this range between the plurality of convex portions 11 (may be different from each other). In a case where the closest distance 6 between the convex portions 11 cannot be less than 0 μm, and is equal to or less than 500 μm, a contact area between the liquid sample and the flow path increases, and thereby the capillary force increases. Therefore, it becomes easier to move the liquid sample. Here, "the closest distance between the convex portions 11" is a closest distance between a pair of adjacent convex portions 11 in the same region.

An aspect ratio of the convex portions 11 constituting the microstructure is preferably equal to or more than 0.1 and equal to or less than 2.0. The aspect ratio mentioned herein is a value (Lh/Lv) obtained by dividing the height (Lh) of the convex portion 11 by a representative length (diameter 5C) (Lv) of a bottom surface 10 of the convex portion 11. The height is preferably 5A (maximum value of the height). In a case where the aspect ratio is equal to or more than 0.1, the contact area between the liquid sample and the flow path increases, and with this, the capillary force increases. Therefore, it becomes easier to move the liquid sample. In a case where the aspect ratio is equal to or less than 2.0, preparation of a microstructure becomes easier.

The entire shape of the membrane carrier is not particularly limited, but may be a polygon such as a square, a circle, or an ellipse. In a case where the membrane carrier is square, the vertical width of the membrane carrier may be equal to or more than 2 mm and equal to or less than 100 mm, for example, and the horizontal width of the membrane carrier may be equal to or more than 2 mm and equal to or less than 100 mm, for example. A thickness of the membrane carrier excluding a height of the microstructure may be equal to or more than 0.1 mm, and equal to or less than 10 mm, for example.

In order to prepare a detection zone in the liquid sample test kit of the present embodiment, it is necessary to immobilize a detection substance in at least a part of the flow path. Depending on the material of the flow path and the kind of the detection substance, there is a possibility that the detection substance cannot be immobilized enough to allow visual determination at a time of detection. In that case, an appropriate surface treatment can be performed only on the detection zone.

The surface treatment technique is not limited at all, and various techniques such as UV irradiation, UV/ozone treatment, various plasma treatments, and surface modification with 3-aminopropyl triethoxysilane or glutaraldehyde can be used, for example.

In the present embodiment, examples of the detection substance include an antibody, for example. The antibody is an antibody that reacts with a substance to be detected by an antigen-antibody reaction, and may be a polyclonal antibody or a monoclonal antibody. Here, the substance to be detected is not limited at all, and may be any substance that can react with an antibody by an antigen-antibody reaction, such as various pathogens and various clinical markers. Specific examples include virus antigens such as influenza virus, norovirus, adenovirus, RS virus, HAV, HBs, and HIV, bacterial antigens such as MRSA, group A streptococcus, group B streptococcus, and genus *Legionella*, toxins produced by bacteria and the like, hormones such as *Mycoplasma, Chlamydia trachomatis*, and human chorionic gonadotropin, C-reactive protein, myoglobin, cardiac troponin, various tumor markers, pesticides, environmental hormones, and the like, but are not limited thereto. In particular, it is particularly useful for items that require urgent detection and treatment such as influenza virus, norovirus, C-reactive protein, myoglobin, and cardiac troponin. The substance to be detected may be an antigen capable of inducing an immune reaction alone, or a hapten not capable of inducing an immune reaction by itself but capable of binding to an antibody by an antigen-antibody reaction.

Regarding the determination by the optical technique, there are mainly two techniques: a determination by visual observation and measurement of the fluorescence intensity. In the case of determination by visual observation, the color difference between the two color stimuli at a time of measuring colors before and after the detection by the color system of the CIE1976L*a*b* color space (ΔE described in JIS Z8781-4: 2013) is preferably equal to or more than 0.5. In a case where the color difference is equal to or more than 0.5, it is easy to visually confirm the difference in color. In a case where the fluorescence intensity is measured and determined, a ratio (S/N ratio) of the fluorescence intensity (FI1) in the detection zone to the fluorescence intensity (FI2) in upstream and downstream regions adjacent to the detection zone is preferably FI1:FI2=10:1 or more. In a case where the ratio is 10:1 or more, separation of signal and noise becomes easy.

EXAMPLES

Hereinafter, the present embodiment will be specifically described, but the present embodiment is not limited to these experimental examples.

Experimental Example 1

<Preparation of Mold>

A mold was prepared by laser processing and mechanical cutting. This mold is made of aluminum alloy A5052. At the center of the mold, a concave portion having a shape formed by connecting two cones illustrated in FIG. 1, in which the depth at the peak position where the diameter (5C in FIG. 1) is 100 μm and the depth (referred to as height in the table in some cases) is minimum (maximum in the table) is (5A in FIG. 1) is 100 μm, the maximum value of the depth in the region between the peak positions (the minimum value in the table) (5B in FIG. 1) is 50 μm, and the maximum value of the depth is present in a downward direction perpendicular to the center point of the circle serving as the bottom surface, is processed in a range of 3 cm×3 cm in a triangular arrangement form of FIG. 1 with the closest distance 6 between the microstructures being 5 μm. The perpendicular feet X, X' of 5A and the perpendicular foot Y of 5B are on the diameter ZW of the bottom surface (circle). A distance (ZX, WX') between the intersection of the circumference and the diameter and the perpendicular foot at the maximum value of the height, and a distance between the perpendicular foot at the maximum value of the height and the perpendicular foot at the minimum value of the height are the same. That is, ZX=XY=YX'=WX'.

The perpendicular foot of 5B (minimum value of the height) is at the center of the bottom surface (circle).

A mold release treatment was performed on an irregular surface of the mold in order to easily and reliably peel off the mold at a time of transfer from thermoplastic plastic. A technique of mold release treatment was carried out by performing immersion by Optool HD-2100TH (manufactured by Daikin Industries, Ltd.) for about 1 minute, drying, and allowing it to stand overnight.

<Transfer of Microstructure>

The microstructure was transferred to a thermoplastic plastic using the mold obtained as described above. As the thermoplastic plastic, polystyrene (Denka styrene sheet manufactured by Denka Corporation, membrane thickness: 300 μm) was used. Thermal imprinting was used as a processing method, and X-300 manufactured by SCIVAX was used as an apparatus. At a molding temperature of 120° C. and an applied pressure of 5.5 MPa, transfer was performed for 10 minutes. After the transfer, the thermoplastic plastic and the mold were cooled to 80° C. while applying pressure, and then the pressure was removed to prepare a membrane carrier having a microstructure illustrated in FIG. 1.

In the prepared membrane carrier, the maximum peak position height, the minimum peak position height, 5B/5A (a ratio of the minimum value 5B of the height in this region and the higher value 5A among the maximum peak positions (maximum value of the height)), and the processing range of the structure having a plurality of peak positions are shown in Table 1. The convex portion is a cone. A thickness of the membrane carrier excluding the height of the microstructure (convex portion) is 0.2 mm.

<Preparation of Detection Zone>

Figure 7:
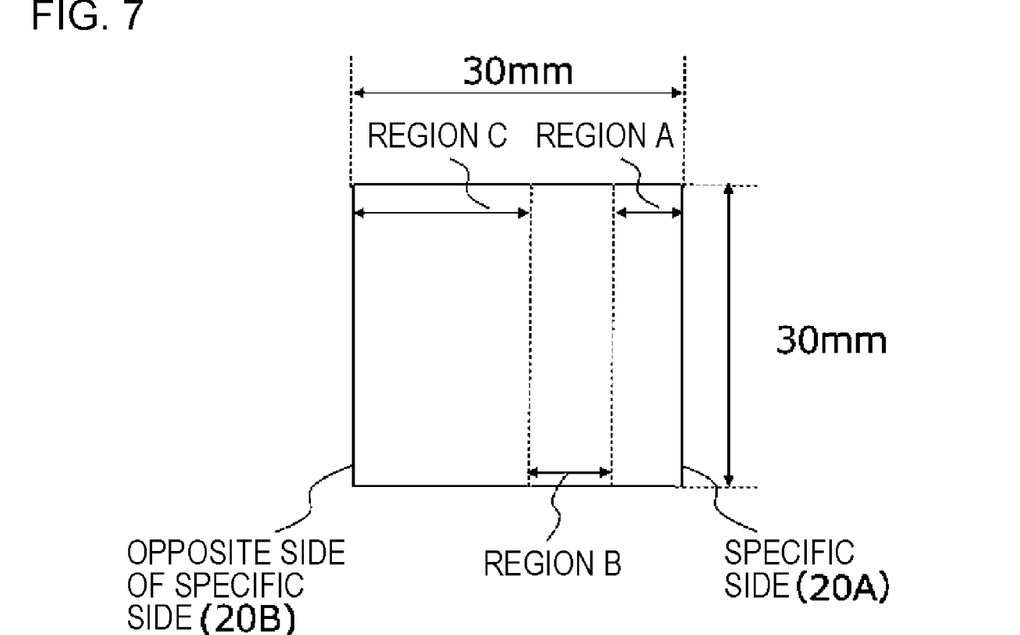
FIG. 7 is an example of an embodiment according to the present invention, and is a schematic bird's-eye view of the membrane carrier.

An anti-type A influenza NP antibody suspension and an anti-type B influenza NP antibody suspension were applied by 3 cm to positions of 0.6 cm and 1.0 cm, respectively, from a specific side (20A) of the membrane carrier of FIG. 7 prepared as described above (the application amount was 3 μL for each) and dried well under warm air to immobilize a detection substance.

<Set of Label Substances>

Purified anti-type A influenza virus NP antibody (another antibody as described above) and purified anti-type B influenza virus NP antibody (another antibody as described above) were used. The anti-type A influenza virus NP antibody is covalently labeled with red latex particles (SC-042-R polystyrene latex particles colored latex particles manufactured by JSR Life Science Corporation) having a particle size of 0.2 μm, the resultant product was suspended in a tris buffer solution containing saccharide, a surfactant, and protein such that a concentration of the latex particles was 0.025 mass % by volume (w/v %), and subjected to ultrasonic treatment to prepare a sufficiently dispersed and suspended anti-type A label. Similarly, an anti-type B label in which blue latex particles were labeled with an anti-type B influenza virus NP antibody was prepared.

The anti-type A label and the anti-type B label were mixed, and applied to a glass fiber (33GLASS NO. 10539766 manufactured by Schleicher & Schuell) having a size of 3 cm×1 cm by an amount of 50 μL per 1 cm² and dried well in warm air to prepare a label pad. Thereafter, a label substance pad was overlapped by 2 mm at the end of the prepared membrane carrier, and cut into strips having a width of 5 mm with a cutter to prepare an integrated liquid sample test kit.

<Detection Evaluation>

100 μL of the liquid sample was dropped on the end of the liquid sample test kit prepared as described above. As the liquid sample, a specimen suspension attached to Quick-Navi-Flu manufactured by Denka Seiken Co., Ltd. was used as a dilution solution. In a case where the dilution rate of type A influenza virus A/Beijing/32/92 (H3N2) was increased from $2\times10^4$, the dilution rate (limit magnification at which type A visual determination is possible), at which the presence or absence of a colored line could not be visually observed 10 minutes after the start of the test, was obtained. In a case of test at a dilution rate of 1/2 of the dilution rate, the time from the start of the start of the test until the color density of the colored line was stabilized (the time until the type A density was stabilized) was obtained as a detection time. The result is shown in Tables 1 and 2.

100 μL of the liquid sample was dropped on the end of the liquid sample test kit prepared as described above. As the liquid sample, a specimen suspension attached to Quick-Navi-Flu manufactured by Denka Seiken Co., Ltd. was used as a dilution solution. In a case where the dilution rate of type B influenza virus B/Shangdong/7/97 was increased from $2\times10^3$, the dilution rate, at which the presence or absence of a colored line could not be visually observed 10 minutes after the start of the test (the limit magnification at which type B visual determination is possible), was obtained. In a case of test at a dilution rate of 1/2 of the dilution rate, the time from the start of the test until the color density of the colored line was stabilized (the time until the type B density became stable) was obtained as a detection time. The result is shown in Tables 1 and 2.

As for the detection time, an average value of the time until the density of the type A was stabilized and the time until the density of the type B was stabilized was used as the detection time.

Experimental Example 2

An experiment was performed under the same conditions as in Experimental Example 1, except that the maximum value (minimum value in the table) of the depth in the region between the peak positions was 25 μm.

Experimental Example 3

An experiment was performed under the same conditions as in Experimental Example 1, except that the maximum value (minimum value in the table) of the depth in the region between the peak positions was 75 μm.

Experimental Example 4

An experiment was performed under the same conditions as in Experimental Example 1, except that the maximum value (minimum value in the table) of the depth in the region between the peak positions was 12.5 μm.

Experimental Example 5

An experiment was performed under the same conditions as in Experimental Example 1, except that the maximum value (minimum value in the table) of the depth in the region between the peak positions was 87.5 μm.

Experimental Example 6

In FIG. 7, in a region (region A) of 5 mm inside the processing range from a specific side (20A) of the processing range in the mold and a region (region C) of 15 mm inside the processing range from the opposite side (20B) of the specific side, concave portions of a cone having a diameter of 100 μm and a depth of 100 μm (also referred to as height in the table) (this cone has only one peak position (apex)) are arranged in line in a triangular arrangement form of FIG. 1 with the closest distance 6 between the microstructures being 5 μm.

In a range other than the above processing range (region B), a mold was prepared in the same manner as in Experimental Example 1. That is, at the center of the mold, a concave portion having a shape formed by connecting two cones illustrated in FIG. 1, in which the depth at the peak position where the diameter (5C in FIG. 1) is 100 μm and the depth (referred to as height in the table in some cases) is minimum (maximum in the table) (5A in FIG. 1) is 100 μm, the maximum value of the depth in the region between the peak positions (the minimum value in the table) (5B in FIG. 1) is 50 μm, and the maximum point of the depth is present in a downward direction perpendicular to the center point of the circle serving as the bottom surface, is processed in a range of 3 cm×3 cm in a triangular arrangement form of FIG. 1 with the closest distance 6 between the microstructures being 5 μm. The perpendicular feet X, X' of 5A and the perpendicular foot Y of 5B are on the diameter ZW of the bottom surface (circle). A distance (ZX, WX') between the intersection of the circumference and the diameter and the perpendicular foot at the maximum value of the height, and a distance between the perpendicular foot at the maximum value of the height and the perpendicular foot at the minimum value of the height are the same. That is, ZX=XY=YX'=WX'. The perpendicular foot of 5B (minimum value of the height) is at the center of the bottom surface (circle).

Other than that, the experiment was performed under the same conditions as in Experimental Example 1.

Experimental Example 7

An experiment was performed under the same conditions as in Experimental Example 1, except that, in the microstructure of Experimental Example 1, a concave, portion of a cone having a diameter of 100 μm and a depth of 100 μm (referred to as height in the table) (this cone has only one peak position (apex)) is arranged in a triangular arrangement form of FIG. 1 with the closest distance 6 between the microstructures being 5 μm.

Experimental Examples 10 to 15

The particles used were changed from colored latex particles to fluorescent latex particles (micromer-F fluorescent latex particles material polystyrene manufactured by Corefront Corporation), and 10 minutes after the start of the test, a magnification (the limit magnification at which fluorescence can be determined), at which the presence or absence of a colored line could not be read with an immunochromatography reader (C11787 manufactured by Hamamatsu Photonics Co., Ltd.), that is, the magnification at which the S/N ratio is equal to or less than 10, was obtained. The other contents were the same as those in Experimental Examples 1 to 6. The membrane carrier of Experimental Example 15 is the same as that of Experimental Example 6.

TABLE 1

|  | Example 1 | Example 2 | Example 3 | Example 4 | Example 5 | Example 6 | Example 7 |
| --- | --- | --- | --- | --- | --- | --- | --- |
| Peak position height which is maximum (μm) | 100 | 100 | 100 | 100 | 100 | 100 | 100 |
| Peak position height which is minimum (μm) | 50 | 25 | 75 | 12.5 | 87.5 | 50 | None |
| 5B/5A | 0.5 | 0.25 | 0.75 | 0.125 | 0.875 | 0.5 | — |
| Processing range of structure having a plurality of peak positions | Entirety | Entirety | Entirety | Entirety | Entirety | Region within range of 5 to 15 mm, from specific side | None |
| Limit magnification at which type A visual determination is possible | $7 \times 10^4$ | $6 \times 10^4$ | $7 \times 10^4$ | $5 \times 10^4$ | $8 \times 10^4$ | $7 \times 10^4$ | $4 \times 10^4$ |
| Limit magnification at which type B visual determination is possible | $7 \times 10^3$ | $6 \times 10^3$ | $7 \times 10^3$ | $5 \times 10^3$ | $8 \times 10^3$ | $7 \times 10^3$ | $4 \times 10^3$ |

TABLE 1-continued

|  | Example 1 | Example 2 | Example 3 | Example 4 | Example 5 | Example 6 | Example 7 |
|---|---|---|---|---|---|---|---|
| Detection time (minute) | 8 | 7 | 9 | 7 | 10 | 7 | 7 |
| Notes | Working Example | Working Example | Working Example | Working Example | Working Example | Working Example | Comparative Example |

Entirety means the entire processing range.

TABLE 2

|  | Example 10 | Example 11 | Example 12 | Example 13 | Example 14 | Example 15 |
|---|---|---|---|---|---|---|
| Peak position height which is maximum (μm) | 100 | 100 | 100 | 100 | 100 | 100 |
| Peak position height which is minimum (μm) | 50 | 25 | 75 | 12.5 | 87.5 | 50 |
| 5B/5A | 0.5 | 0.25 | 0.75 | 0.125 | 0.875 | 0.5 |
| Processing range of structure having a plurality of peak positions | Entirety | Entirety | Entirety | Entirety | Entirety | Region within range of 5 to 15 mm, from specific side |
| Limit magnification at which type A visual determination is possible 10 minutes after start of test | $4 \times 10^6$ | $3 \times 10^6$ | $3 \times 10^6$ | $2 \times 10^6$ | $2 \times 10^4$ | $4 \times 10^4$ |
| Limit magnification at which type B visual determination is possible 10 minutes after start of test | $4 \times 10^5$ | $3 \times 10^5$ | $3 \times 10^5$ | $2 \times 10^5$ | $2 \times 10^3$ | $4 \times 10^3$ |
| Notes | Working Example | Working Example | Working Example | Working Example | Working Example | Working Example |

Entirety means the entire processing range.

From the results in Tables 1 and 2, it was shown that the liquid sample test kit according to the present embodiment can perform a highly sensitive test by providing a plurality of height peak positions in the microstructure in the flow path.

An object of the present embodiment is to provide a test kit capable of performing highly sensitive determination in an immunochromatography method capable of optically confirming that a substance to be detected is detected. Since the liquid sample test kit of the present embodiment can perform a highly sensitive test at low cost, it is useful as a disposable POCT reagent.

In this application, priority is claimed on Japanese Patent Application No. 2017-236605, filed on Dec. 11, 2017, the content of which is incorporated herein by reference.

REFERENCE SIGNS LIST

1: flow direction of liquid sample (transporting direction)
1A: flow traveling in gap between structures
1B: flow traveling in gap at peak position
2: flow path
3: membrane carrier
3x: dropping zone
3y: detection zone
5: height of microstructure
5A: height of microstructure at peak position
5A': height of microstructure at peak position
5B: height of microstructure at minimum value between peak positions
5C: diameter of microstructure
6: closest distance between microstructures (closest distance)
11: convex portion
18: test kit
18a: housing
18b: first opening
18c: second opening
20A: specific side
20B: opposite side of specific side
W: intersection of circumference and diameter of bottom surface (circle)
X: perpendicular foot of 5A (maximum value of height)
X': perpendicular foot of 5A (maximum value of height)
Y: perpendicular foot of 5B (minimum value of height)
Z: intersection of circumference and diameter of bottom surface (circle)

The invention claimed is:

1. A membrane carrier for a liquid sample test kit that detects a substance to be detected in a liquid sample, the membrane carrier comprising:
at least one integrally-molded flow path capable of transporting the liquid sample,
wherein a plurality of microstructures that cause a capillary action for transporting the liquid sample are provided on a bottom surface of the flow path,
wherein each microstructure of the plurality of microstructures is a structure having two or more peak positions,
wherein a maximum height is the height at the peak positions as determined from the bottom surface of the flow path, wherein a minimum height is a minimum value in a region between the peak positions in the microstructure as determined from the bottom surface of the flow path, wherein the minimum height is equal to or more than ⅛ and equal to or less than ⅞ of the maximum height, and wherein the plurality of microstructures are provided apart from each other in a long-side direction of the membrane carrier.

2. The membrane carrier for a liquid sample test kit according to claim 1, wherein the structure having two or more peak positions at which a height becomes maximum per one repeating unit structure is provided only in a portion of the flow path.

3. The membrane carrier for a liquid sample test kit according to claim 1, further comprising:

a detection zone for detecting the substance to be detected in the liquid sample.

4. The membrane carrier for a liquid sample test kit according to claim 3, wherein, in a case where the substance to be detected is detected in the detection zone, the detection can be confirmed by an optical technique.

5. The membrane carrier for a liquid sample test kit according to claim 1, wherein a label having an antibody specifically reacting with the substance to be detected in the liquid sample or an antigen-binding fragment thereof is provided in at least a portion of the membrane carrier for a liquid sample test kit so as to react with the substance to be detected, and wherein means capable of being confirmed by an optical technique is a change in color, and the change in color occurs by the label bound to the substance to be detected.

6. The membrane carrier for a liquid sample test kit according to claim 5, wherein the label is a particle to which the antibody or the antigen-binding fragment is bound.

7. The membrane carrier for a liquid sample test kit according to claim 6, wherein the particle is at least one kind from the group consisting of a colored latex particle and a fluorescent latex particle.

8. A membrane carrier for a liquid sample test kit that immobilizes, in a detection zone of the membrane carrier for a liquid sample test kit according to claim 3, a detection substance causing a change in color capable of confirming the detection by an optical technique, in a case where a substance to be detected is detected in the detection zone.

9. A liquid sample test kit comprising the membrane carrier for a liquid sample test kit according to claim 1.

10. A membrane carrier that detects a substance to be detected in a liquid sample, comprising:

a flow path capable of transporting the liquid sample, wherein a plurality of microstructures are provided on a bottom surface of the flow path, wherein each microstructure of the plurality of microstructures is a structure having two or more peak positions, wherein a maximum height is the height at the peak positions of the microstructure as determined from the bottom surface of the flow path, wherein a minimum height is a minimum value in a region between the peak positions in the microstructure as determined from the bottom surface of the flow path, wherein the minimum height is equal to or more than ⅛ and equal to or less than ⅞ of the maximum height, and wherein the plurality of microstructures are provided apart from each other in a long-side direction of the membrane carrier.

* * * * *